United States Patent
Tang et al.

(10) Patent No.: US 7,645,994 B2
(45) Date of Patent: Jan. 12, 2010

(54) DEVICE FOR OUTPUTTING HIGH AND/OR LOW ENERGY X-RAYS

(75) Inventors: Chuanxiang Tang, Beijing (CN); Huaibi Chen, Beijing (CN); Yinong Liu, Beijing (CN); Jianping Cheng, Beijing (CN); Yaohong Liu, Beijing (CN); Renkai Li, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 246 days.

(21) Appl. No.: 11/647,543

(22) Filed: Dec. 28, 2006

(65) Prior Publication Data

US 2007/0170375 A1    Jul. 26, 2007

(30) Foreign Application Priority Data

Dec. 31, 2005 (CN) .................. 2005 1 0135933

(51) Int. Cl.
| | |
|---|---|
| H01L 27/146 | (2006.01) |
| H01J 23/34 | (2006.01) |
| H01J 5/18 | (2006.01) |
| H05H 7/00 | (2006.01) |

(52) U.S. Cl. .................. 250/370.09; 250/492.3; 250/494.1; 313/359.1; 378/140; 315/500; 315/505; 315/111.81

(58) Field of Classification Search ............ 250/370.09, 250/492.3, 493.1, 494.1, 503.1; 313/360.1, 313/359.1, 363.1; 315/5.39, 5.41, 5.42, 500, 315/505, 111.01, 111.61, 111.81; 378/119, 378/140
See application file for complete search history.

(56) References Cited

U.S. PATENT DOCUMENTS

| | | | | | |
|---|---|---|---|---|---|
| 4,260,885 | A | * | 4/1981 | Albert | 378/45 |
| 4,484,339 | A | * | 11/1984 | Mallozzi et al. | 378/82 |
| 4,595,834 | A | * | 6/1986 | Burns | 250/374 |
| 5,039,910 | A | * | 8/1991 | Moriguchi et al. | 315/5.41 |
| 5,051,600 | A | * | 9/1991 | Schuetz et al. | 250/492.3 |
| 5,401,973 | A | * | 3/1995 | McKeown et al. | 250/492.3 |
| 5,646,477 | A | * | 7/1997 | Yamagishi | 313/365 |
| 5,689,540 | A | * | 11/1997 | Stephenson et al. | 378/53 |
| 6,407,505 | B1 | * | 6/2002 | Bertsche | 315/5.41 |
| 6,456,690 | B2 | * | 9/2002 | Yamada et al. | 378/119 |
| 6,548,810 | B2 | * | 4/2003 | Zaluzec | 850/9 |
| 6,646,383 | B2 | * | 11/2003 | Bertsche et al. | 315/5.41 |

(Continued)

*Primary Examiner*—Bernard E Souw
(74) *Attorney, Agent, or Firm*—Westman, Champlin & Kelly, P.A.

(57) ABSTRACT

Disclosed is a device for outputting high and/or low energy X-rays, in which the electron gun power supply provides power to the electron linear accelerating tube under the control of the control system; the microwave power source accelerates electron beams generated by the electron linear accelerating tube under the control of the control system; the electron linear accelerating tube is connected to the electron gun power supply and the microwave power source respectively, to generate high energy electron beams; the high-voltage electron gun power supply provides power to the high-voltage electron gun under the control of the control system; the high-voltage electron gun is connected to the voltage electron gun power supply to generate low energy electron beams; the radiation target receives the high energy electron beams to generate high energy transmission X-rays, and/or receive the low energy electron beams to generate low energy reflection X-rays. The present invention can be applied in the radiotherapy and the medical imaging, or can be applied in the nondestructive inspection.

8 Claims, 4 Drawing Sheets

U.S. PATENT DOCUMENTS

| | | | |
|---|---|---|---|
| 6,914,959 B2 * | 7/2005 | Bailey et al. | 378/65 |
| 7,227,925 B1 * | 6/2007 | Mansfield et al. | 378/65 |
| 2002/0158575 A1 * | 10/2002 | Bertsche et al. | 313/505 |
| 2002/0191746 A1 * | 12/2002 | Dinsmore | 378/119 |
| 2003/0048868 A1 * | 3/2003 | Bailey et al. | 378/65 |
| 2005/0117683 A1 * | 6/2005 | Mishin et al. | 376/157 |
| 2005/0163284 A1 * | 7/2005 | Inazuru | 378/108 |
| 2006/0233307 A1 * | 10/2006 | Dinsmore | 378/136 |
| 2007/0165784 A1 * | 7/2007 | Nakanishi et al. | 378/119 |
| 2007/0170375 A1 * | 7/2007 | Tang et al. | 250/493.1 |
| 2007/0269013 A1 * | 11/2007 | Liu et al. | 378/119 |

* cited by examiner

A device for outputting high and/or low energy X-rays

DEVICE FOR OUTPUTTING HIGH AND/OR LOW ENERGY X-RAYS

The present application claims priority of Chinese patent application Serial No. 200510135933.2, filed Dec. 31, 2005, the content of which is hereby incorporated by reference in its entirety.

FIELD OF THE INVENTION

The present invention relates to an X-ray source, and more particularly, to a device for outputting high and/or low energy X-rays.

BACKGROUND OF THE INVENTION

An electron linear accelerator may generate high energy electron beams or thus generate X-rays by having high energy electron beams hit a target. The radiotherapy is a processing technology that makes an irradiated article generate certain biological and physical effects by means of the ionization capability and the Bremsstrahlung effect of electron beams or X-rays, thereby treating tumors. Generally, in the radiotherapy, the focus area of a patient is firstly imaged and located with an analog localizer, and the radiation therapy is conducted with regard to the set therapy area based on the imaging-located results by an electron linear accelerator. According to the current demand, it is desired that the imaging and the radiotherapy could be achieved without moving the patient. For this demand, the prior arts mainly had the X-ray machine and the linear accelerator mounted at different angles of the Gantry or at different places of the treatment room respectively to perform the imaging and the radiotherapy without moving the patient. Some deviations would occur due to the different imaging angles and the different radiotherapy angles. Additionally, X-rays generated by low energy electron beams were used to conduct the imaging and high energy electron beams or the X-rays were used to conduct the radiotherapy by means of the energy switching technology of the electron linear accelerator. However, in this case, the quality of the imaging is poor because it is difficult for the low energy electron beams to be lower than 100 KeV.

The nondestructive inspection technique is to inspect the internal construction of an object by means of the penetration capacity of X-rays to the object. Recently, it is proposed to employ X-rays of two energy spectra, which are generated by electron beams having two levels of energy hit a target, to alternately conduct the radiation imaging with regard to the inspected object, and thereby identify the material features of object. This application needs a quick switching of the energy of the electron beams, and requires the energy difference between electron beams to be as large as possible. In the prior art, the quick adjustment of the energy of the electron beams generally was carried out by changing power and frequency of microwaves and the load of electron beams. In this case, the adjustment range of the electron beams is limited and the imaging quality deteriorates.

SUMMARY OF THE INVENTION

An object of the present invention is to provide a device for outputting high and/or low energy X-rays, by which the imaging quality is good and the adjustment range of electron beams is large.

According to the present invention, there is provided a device for outputting high and/or low energy X-rays, comprising a control system, an electron gun power supply, a high-voltage electron gun power supply, a microwave power source, an electron linear accelerating tube, a high-voltage electron gun and a radiation target, wherein the electron gun power supply powers the electron linear accelerating tube under the control of the control system; the microwave power source accelerates electron beams generated by the electron linear accelerating tube under the control of the control system; the electron linear accelerating tube is connected to the electron gun power supply and the microwave power source respectively, to generate high energy electron beams; the high-voltage electron gun power supply powers the high-voltage electron gun under the control of the control system; the high-voltage electron gun is connected to the voltage electron gun power supply to generate low energy electron beams; the radiation target receives the high energy electron beams to generate high energy transmission X-rays, and/or receives the low energy electron beams to generate low energy reflection X-rays.

Preferably, the electron linear accelerating tube comprises an electron gun which generates electron beams driven by the electron gun power supply, and an accelerating apparatus for accelerating the electron beams.

Preferably, an angle between an output direction of electron beams from the electron linear accelerating tube and an output direction of electron beams from the high-voltage electron gun is set in a range of 85 degree to 95 degree.

Preferably, an output direction of electron beams from the electron linear accelerating tube is perpendicular to an output direction of electron beams from the high-voltage electron gun.

Preferably, a radiation direction of the high energy transmission X-rays is the same as that of the low energy reflection X-rays.

Preferably, the high-voltage electron gun is provided with a transmitting tube for the low energy electron beams, which has an X-ray output window.

Preferably, the X-ray output window is made of material having a small absorptivity for high and/or low energy X-rays.

Preferably, the material is titanium.

Preferably, the transmitting tube is positioned on the X-ray output window to be concave toward a target point on the radiation target.

Preferably, the high energy electron beams are pulsed and the low energy electron beams are continuous or pulsed.

With the above configuration, it is possible to adjust the X-ray energy in a larger range comparing with the prior art, and conduct more clear imaging with low energy reflection X-rays that were generated by electron beams of tens KeVs or hundreds KeVs hitting the target, and then conduct the radiotherapy with X-rays generated by electron beams having the energy level of MeVs. The high and/or low energy X-rays of the present invention can both be pulsed, and can achieve the alternate switching between the high and low energy X-ray pulses. The device according to the present invention has simple construction and low cost, and is adapted to be used in various linear accelerator devices.

Figure 1:
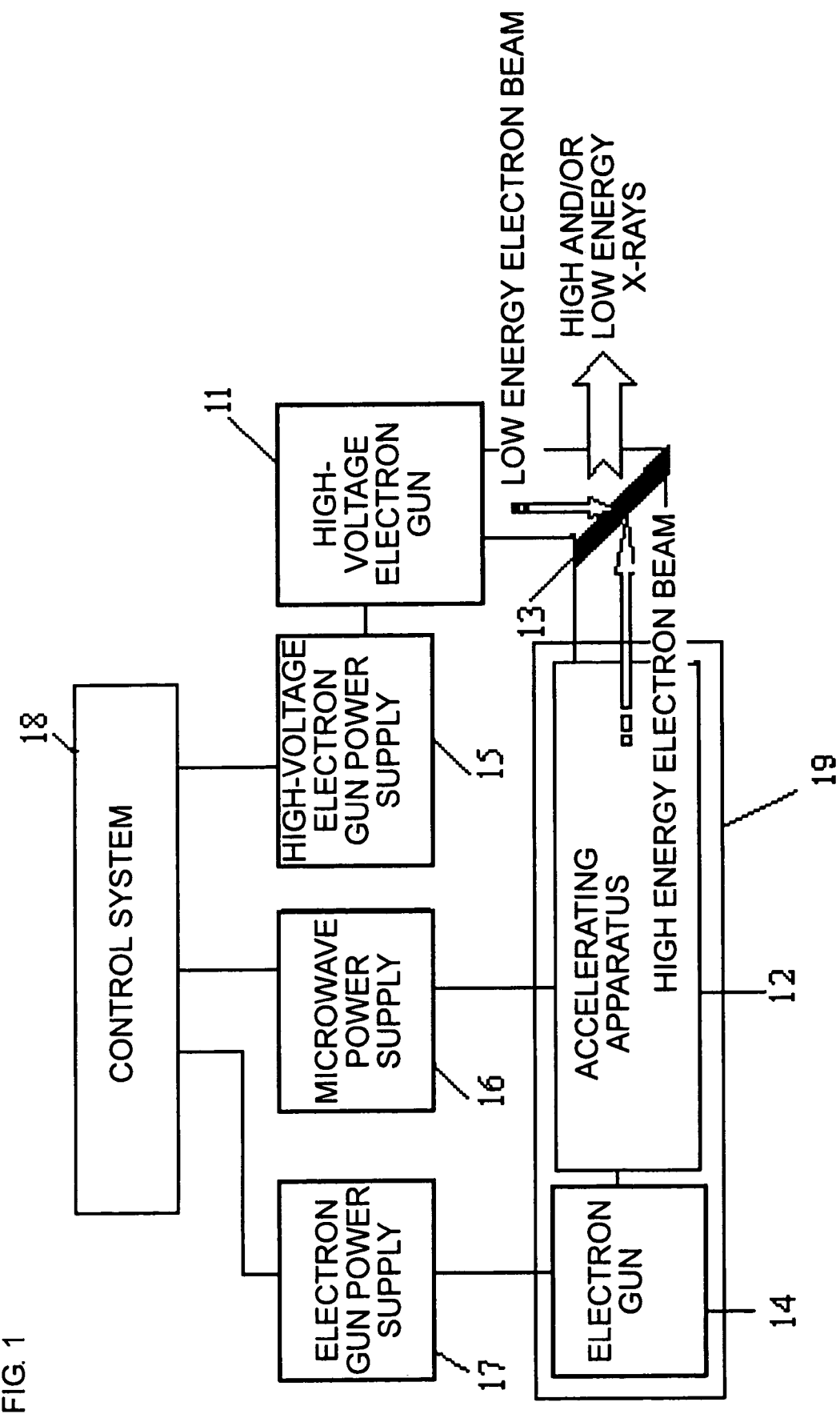
FIG. 1 is a schematic diagram showing the configuration of a device for outputting high and/or low energy X-rays according to an embodiment of the invention.

REFERENCE NUMERAL LIST 11 high-voltage electron gun
12 accelerating apparatus
13 radiation target
14 electron gun
15 high-voltage electron gun power supply
16 microwave power source
17 electron gun power supply
18 control system
19 electron linear accelerating tube
31 X-ray output window
32 transmission tube for low energy electron beams

DETAILED DESCRIPTION OF THE PREFERRED EMBODIMENTS

It is noted that the following embodiments are used only to explain the present invention, but by no means to limit the scope of the present invention.

FIG. 1 is a schematic diagram showing the configuration of a device for outputting high and/or low energy X-rays according to an embodiment of the invention.

Referring to FIG. 1, in a device for outputting high and/or low energy X-rays, an electron linear accelerating tube 19 constituted by an electron gun 14 and an accelerating apparatus 12 is a high energy electron beam generating apparatus, and the generated high energy electron beams hit the radiation target 13 disposed downstream of a high-voltage electron gun 11 and the accelerating apparatus 12, so that high energy transmission X-rays are generated at the right side of the radiation target 13. An low energy electron beams generating apparatus is constituted by the high-voltage electron gun 11 and a high-voltage electron gun power supply 15 thereof, and the generated low energy electron beams hit the right side of the radiation target 13 so that reflection X-rays are generated at the same side. Therefore, the high energy transmission X-rays and low energy reflection X-rays can be generated by hitting the radiation target 13 with electron beams having different energy levels. Although FIG. 1 shows the high energy X-rays and the low energy X-rays travel in the same direction, they can be outputted in different directions by adjusting the relative positions of high-voltage electron gun 11, the accelerating apparatus 12 and the radiation target 13 on the basis of various applications.

The control system 18 may control an electron gun power supply 17 and a microwave power source 16 to generate high energy pulsed electron beams through an electron gun 14 and the accelerating apparatus 12. Or, the control system 18 may control the high-voltage electron gun power supply 15 to drive the high-voltage electron gun 11 to generate continuous or pulsed low energy electron beams.

In addition, the control system 18 may control a timing of the generation of high and/or low energy electron beams. For example, the control system 18 may control the timing to alternatively generate high energy and low energy X-rays for nondestructive inspection, or successively generate continuous low energy X-rays for imaging and then successively generate high energy X-rays for radiotherapy.

Figure 2:
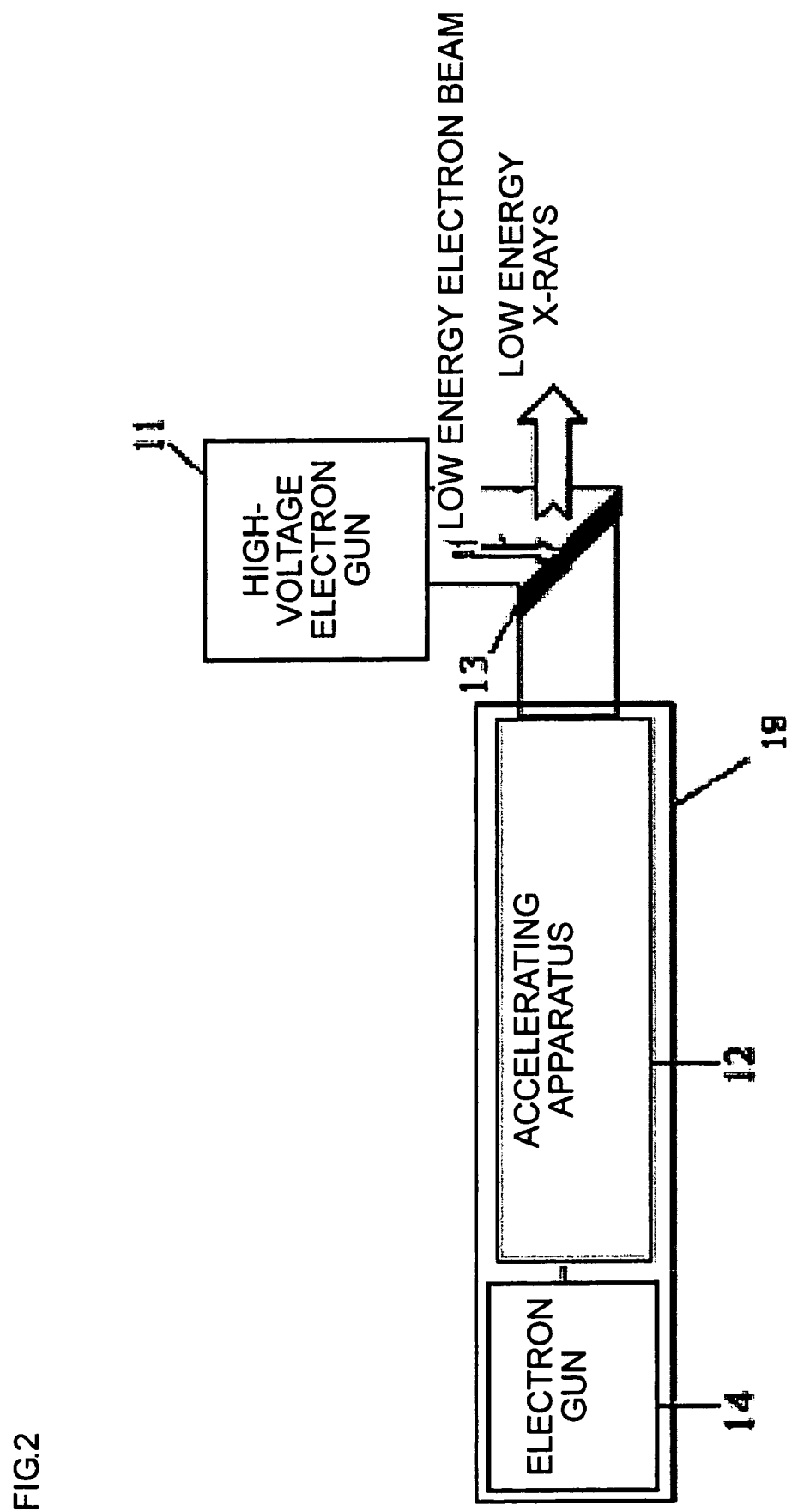
FIG. 2 is a schematic diagram showing the operation of the device for outputting high and/or low energy X-rays under a low energy X-ray operating state.

FIG. 2 is a schematic diagram showing the operation of the device for outputting high and/or low energy X-rays under a low energy X-ray operating state.

Referring to FIG. 2, the device according to the present invention can produce low energy X-rays. In this case, on the basis of the predetermined timing, the control system 18 controls the high-voltage electron gun power supply 15 to drive high-voltage electron gun 11 to generate low energy electron beams. The low energy electron beams generated from the high-voltage electron gun 11 hit a surface of the radiation target 13. Due to low energy, the low energy electron beams are reflected at a surface of the radiation target 13 to generate low energy X-rays which travel in the outgoing direction.

Figure 3:
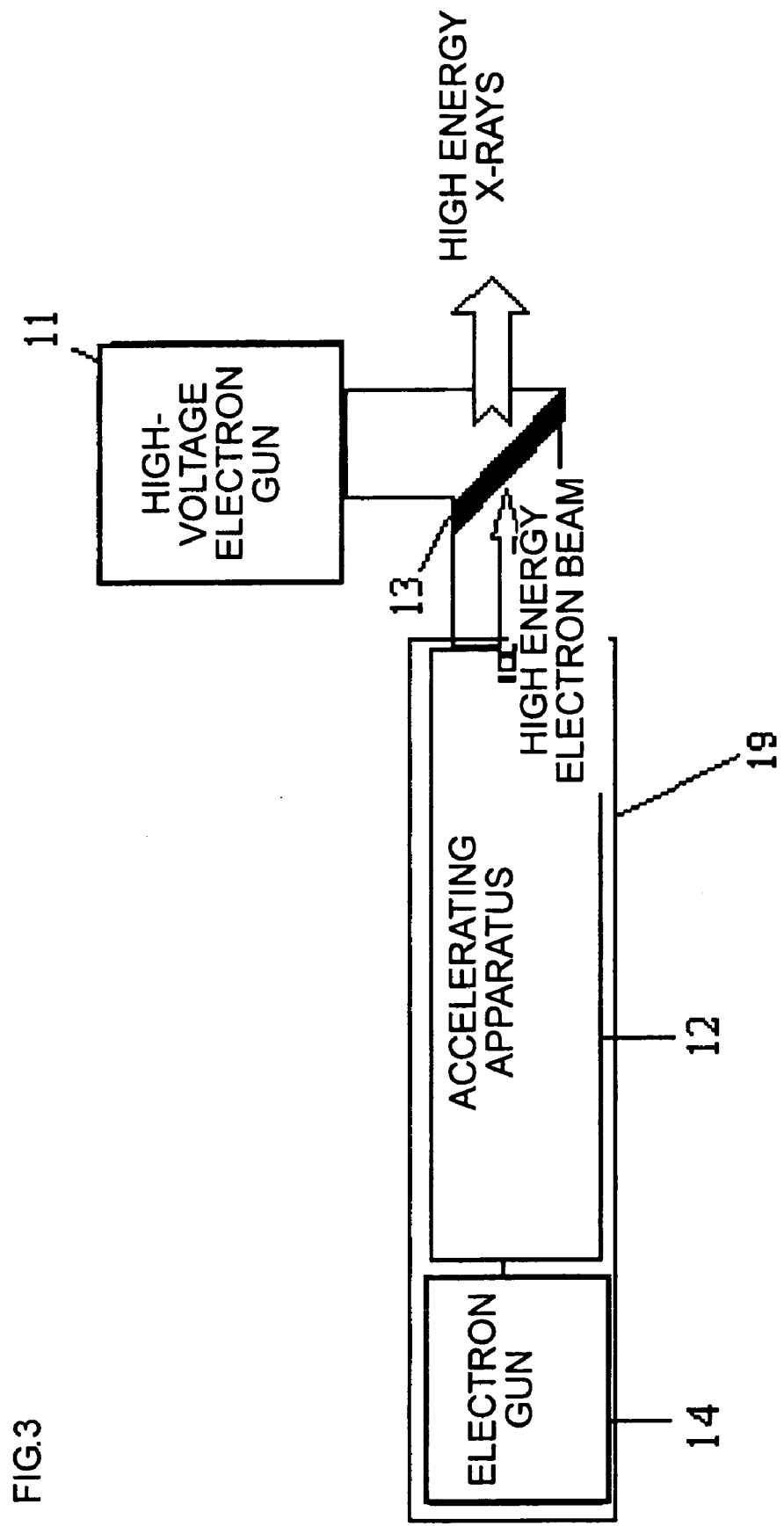
FIG. 3 is a schematic diagram showing the operation of the device for outputting high and/or low energy X-rays under a high energy X-ray operating state.

FIG. 3 is a schematic diagram showing the operation of the device for outputting high and/or low energy X-rays under a high energy X-ray operating state. Referring to FIG. 3, the device according to the present invention can produce high energy X-rays. In this case, on the basis of the predetermined timing, the control system 18 may control electron gun power supply 17 to drive electron gun 14 to generate electron beams to be accelerated, which are inputted into the accelerating apparatus 12. Meanwhile, the control system may control microwave power supply 16 to drive the accelerating apparatus 14 to accelerate the inputted electron beams and generate high energy electron beams. The high energy electron beams generated from the accelerating apparatus 14 hit the radiation target 13 to output high energy X-rays in a transmission direction. As described above, the electron linear accelerating tube 19 can be arranged to be perpendicular to the high-voltage electron gun 11 so that the radiation direction of the high energy X-rays is the same as that of the low energy X-rays. However, an angle between the output direction of low energy electron beams generated from the electron linear accelerating tube 19 and the output direction of high energy electron beams generated from the high-voltage electron gun 11 can be adjusted in a certain range such as a range of 85 degree to 95 degree.

Figure 4:
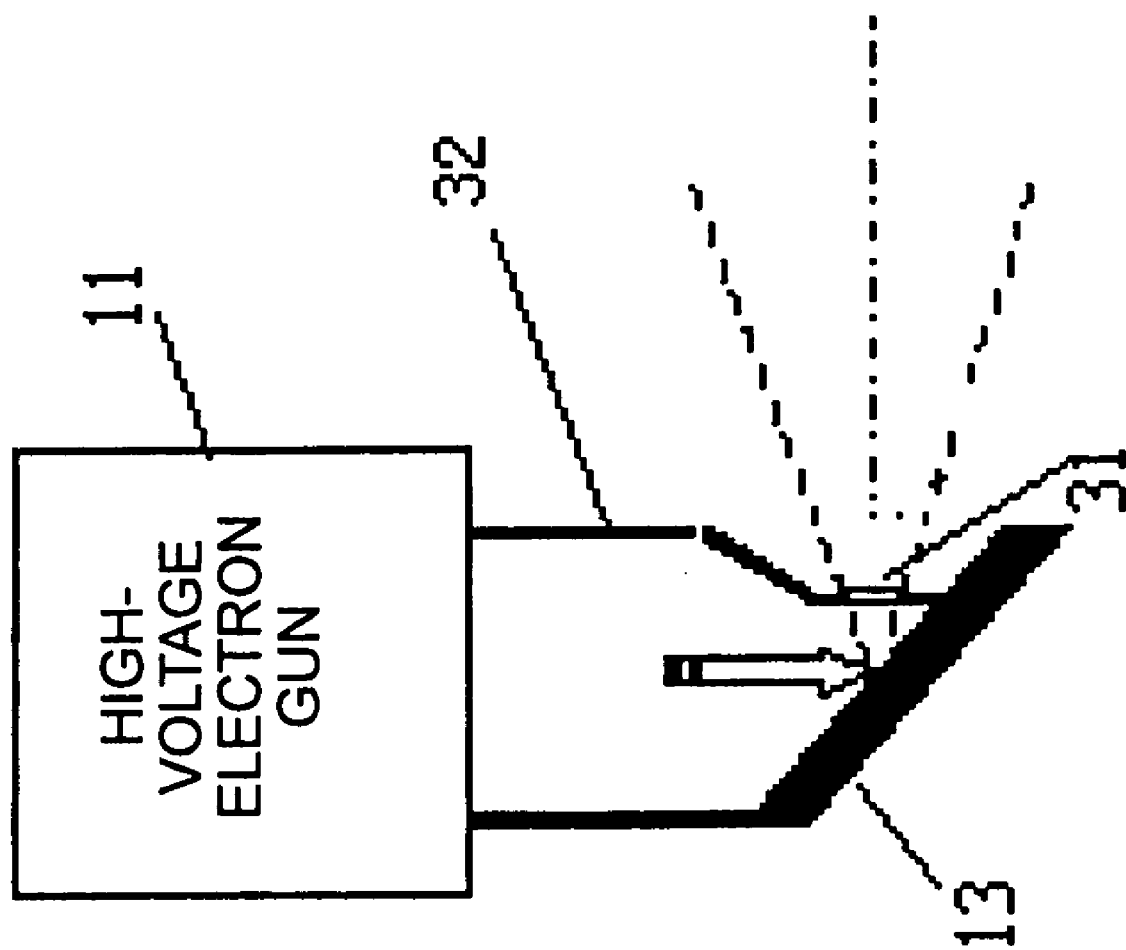
FIG. 4 is a structure schematic diagram showing an X-ray output window included in the device for outputting high and/or energy X-rays.

FIG. 4 is a structure schematic diagram showing an X-ray output window included in the device for outputting high and/or energy X-ray. Referring to FIG. 4, according to an embodiment of the invention, an X-ray output window 31 is arranged on the way the high and/or low energy X-rays travel. The X-ray output window 31 is made of titanium or other material which absorbs less low energy and high energy X-rays or has structures capable of reducing the absorption for the high and/or low energy X-rays. In this embodiment, the X-ray output window 31 is arranged as close to a target point at which the high and/or low energy electron beams hit, as possible in order to reduce the area of the X-ray output window 31 and lower the process difficulty. As shown in FIG. 4, a transmitting tube 32 for the low energy electron beams can be arranged to be concave toward the target point at the X-ray outputting position.

The present invention can be applied in the devices of radiotherapy and the medical imaging, or can be applied in the nondestructive inspection. The present invention has simple construction and low cost, and can be adapted to be widely used in almost all of the linear accelerator devices.

It should be noted that the similar technical solutions obtained by the electron accelerator replaced with other high energy electron generators should be construed as falling into the protection scope of the present invention.

What is claimed is:

1. A device of outputting high and/or low energy X-rays, comprising a control system, an electron gun power supply, a high-voltage electron gun power supply, a microwave power source, an electron linear accelerating tube, a high-voltage electron gun and a radiation target, wherein the electron gun power supply powers the electron linear accelerating tube under the control of the control system;

the microwave power source accelerates electron beams generated by the electron linear accelerating tube under the control of the control system;

the electron linear accelerating tube is connected to the electron gun power supply and the microwave power source respectively, to generate high energy electron beams;

the high-voltage electron gun power supply powers the high-voltage electron gun under the control of the control system;

the high-voltage electron gun is connected to the voltage electron gun power supply to generate low energy electron beams;

the radiation target accepts the high energy electron beams to generate high energy transmission X-rays, and accept the low energy electron beams to generate low energy reflection X-rays;

wherein the high-voltage electron gun is provided with a transmitting tube for the low energy electron beams, which has an X-ray output window a radiation direction of the high energy transmission X-rays is the same as that of the low energy reflection X-rays.

2. The device according to claim 1, wherein the electron linear accelerating tube comprises a electron gun which generates electron beams under the derive of the electron gun power supply, and an accelerating apparatus for accelerating the electron beams.

3. The device according to claim 1, wherein an angle between an output direction of electron beams from the electron linear accelerating tube and an output direction of electron beams from the high-voltage electron gun is set in a range of from 85 degree to 95 degree.

4. The device according to claim 3, wherein an output direction of electron beams from the electron linear accelerating tube is perpendicular to an output direction of electron beams from the high-voltage electron gun.

5. The device according to claim 1, wherein the X-ray output window is made of material which absorbs less low energy X-rays and high energy X-rays.

6. The device according to claim 5, wherein the material comprises titanium.

7. The device according to claim 1 wherein the transmitting tube is positioned on the X-ray output window to be concave toward a target point on the radiation target.

8. The device according to claim 1, wherein the high energy electron beams are pulsed and the low energy electron beams are continuous or pulsed.

* * * * *

UNITED STATES PATENT AND TRADEMARK OFFICE
CERTIFICATE OF CORRECTION

PATENT NO. : 7,645,994 B2
APPLICATION NO. : 11/647543
DATED : January 12, 2010
INVENTOR(S) : Tang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this

Sixteenth Day of November, 2010

David J. Kappos
*Director of the United States Patent and Trademark Office*